United States Patent [19]

Schach et al.

[11] Patent Number: 5,498,807
[45] Date of Patent: Mar. 12, 1996

[54] PROCESS FOR THE PREPARATION OF AROMATIC FLUORO COMPOUNDS

[75] Inventors: Thomas Schach, Gernsheim; Theodor Papenfuhs, Frankfurt, both of Germany

[73] Assignee: Hoechst Aktiengesellschaft, Germany

[21] Appl. No.: 336,474

[22] Filed: Nov. 9, 1994

Related U.S. Application Data

[63] Continuation-in-part of Ser. No. 154,257, Nov. 18, 1993, abandoned.

[30] Foreign Application Priority Data

Nov. 18, 1992 [DE] Germany .......................... 42 38 864.3
Feb. 11, 1994 [DE] Germany .......................... 44 04 343.0

[51] Int. Cl.$^6$ .................................................. C07C 25/13
[52] U.S. Cl. .................... 570/127; 570/123; 570/124; 570/128
[58] Field of Search ................................ 570/142, 143, 570/127, 124, 123

[56] References Cited

U.S. PATENT DOCUMENTS

| | | | |
|---|---|---|---|
| 2,725,405 | 11/1955 | Britton et al. | 570/143 |
| 4,847,442 | 7/1989 | Nalelwajek et al. | 570/142 |
| 4,885,415 | 12/1989 | Marhold et al. | 570/144 |
| 4,937,395 | 6/1990 | Litterer et al. | 570/143 |
| 4,962,246 | 10/1990 | Marhold et al. | 570/127 |
| 5,091,580 | 2/1992 | Pews et al. | 564/407 |
| 5,264,094 | 11/1993 | Sistig et al. | 570/143 |

FOREIGN PATENT DOCUMENTS

| | | |
|---|---|---|
| 2103303 | 5/1994 | Canada . |
| 0302326 | 2/1989 | European Pat. Off. . |
| 0371563 | 6/1990 | European Pat. Off. . |
| 0598338 | 5/1994 | European Pat. Off. . |
| 3824141 | 1/1990 | Germany . |
| 3935862 | 5/1991 | Germany . |
| 1-283230 | 11/1989 | Japan . |
| 3-77836 | 4/1991 | Japan . |
| 4224535 | 8/1992 | Japan ........................ 570/143 |

OTHER PUBLICATIONS

Chemical Abstracts, vol. 115, No. 15, Oct. 14, 1991, Columbus, Ohio, Abstract No. 158695.

Aromatic Fluorine Chemistry, Part 2, Preparation of Chlorofluorobenzenes via fluorination of dichlorobenzenes with KF, R. G. Pews and J. A. Gall, Apr. 28, 1990, pp. 371–374.

*Primary Examiner*—Werren B. Lone
*Attorney, Agent, or Firm*—Connolly & Hutz

[57] ABSTRACT

The invention relates to a process for the preparation of aromatic fluoro compounds of the formula I $$F_nArR^1R^2R^3 \qquad (I)$$

in which Ar is phenyl, naphthyl or pyridyl, $R^1$, $R^2$ and $R^3$ independently of one another are hydrogen, halide, $(C_1–C_4)$-alkyl, phenyl, $NR_2$, OR, CN, COH or COR, where R is hydrogen or $(C_1–C_6)$-alkyl, and n=1, 2, 3, 4 or 5, which comprises reacting aromatic fluoro compounds of the formula II $$X_mF_nArR^1R^2R^3 \qquad (II)$$

in which Ar, $R^1$, $R^2$, $R^3$ and n have the abovementioned meaning, each X is a chlorine or bromine atom and m=1, 2, 3, 4 or 5, with hydrogen in the presence of a palladium catalyst, a water-insoluble amine which also does not form water-soluble hydrohalides, and if desired an inert solvent.

25 Claims, No Drawings

PROCESS FOR THE PREPARATION OF AROMATIC FLUORO COMPOUNDS

This application is a continuation-in-part of U.S. application Ser. 154,257 filed Nov. 18, 1993, abandoned.

DESCRIPTION

Process for the preparation of aromatic fluoro compounds

The present invention relates to an improved process for the preparation of fluorobenzenes by catalytic elimination of halogen from bromine- and/or chlorine-containing fluorobenzenes.

Aromatic fluoro compounds are widely used in the plant protection field and as building blocks in the synthesis of pharmaceutical precursors.

Using electrophilic and nucleophilic substitution, and depending on their existing substitution pattern, aromatic compounds can only be substituted further at quite specific positions. However, when synthesizing aromatic compounds it is often the case that the introduction of a substituent is required precisely at the less preferred positions. There now exists a range of strategies to solve this problem. For instance, unwanted positions in the aromanic compound can be blocked with substituents which, on the one hand, are easily inserted into the molecule and, on the other hand, can be just as easily removed again. Substituents of choice are the halogens bromine and chlorine, which are very easy to introduce by electrophilic substitution into an aromatic system, which block this position in the molecule against further attack, which may have a favorable effect on the electronic conditions for the entry of further substituents in the molecule, and which can be eliminated with ease at the end of the synthetic sequence.

A particularly simple method of introducing fluorine into a molecule is via the corresponding nitro compounds which, because of their high degree of activation for nucleophilic substitutions, enable high selectivities and yields in halex reactions. Where the nitro functions are no longer required in the end product, they have to be removed at the end of the synthesis. The conventional method is via the aniline intermediate stage, with reductive deamination yielding the desired aromatic compounds. In addition to measures connected with the process which in some cases are complex (for example against corrosion), the selectivities and yields achieved are usually no more than moderate. Also, only unfavorable space-time yields can be achieved and high costs in terms of materials are necessary if hydrophosphorous acid is used as reducing agent.

If fluorinated nitro compounds are to be used as advantageous precursors in the synthesis of aromatic fluoro compounds which do not ultimately contain a nitrogen function, the nitro function can be removed again via the synthetic sequence comprising denitrating chlorination followed by reductive dechlorination.

As well as these examples, a large number of other possible uses are conceivable for the reductive elimination of halogen. For example, the halogenation of aromatic fluoro compounds gives not only the desired isomers but also secondary compounds, which may—especially in the case of very expensive fluoro compounds—be the cause of high costs if there is no use for these compounds. In these cases, too, reductive dehalogenation can be used as the method of choice in order, by removing the halogen atoms, to recover expensive starting compounds.

The synthesis of pure fluorobenzenes, in particular, is able to employ reductive dehalogenation as the method of choice for elegant preparation of the corresponding fluorobenzenes by way of easily prepared chlorinated fluoro compounds (which are accessible, for example, by denitrating chlorination of the corresponding fluorinated nitro compounds). Direct halex synthesis starting from the corresponding chloro compounds is generally unsuccessful or succeeds only with very poor selectivities and yields, since under the required reaction temperatures and conditions the end products are in most cases only stable for a short time (Pews, R. G.; Gall, J. A.; J. Fluorine Chem., 50(3), 371–5; EP 371 563).

An alternative method of preparing aromatic fluoro compounds is via the amine diazotization route, of which different variants include the Schiemann and Balz-Schiemann reaction (JP 01 283 230). The technique of amine diazotization with HF has already reached the large industrial scale for some compounds, but can only be applied to specific anilines as starting substance. If deamination with HF is unsuccessful, the somewhat more universal method can be employed of the intermediate isolation of tetrafluoroborates and their subsequent decomposition to give the appropriate aromatic fluoro compounds. Reactions of this type are difficult to manage on an industrial level, and the low yields and space-time yields result in high production costs.

Reductive dehalogenation is thus of very great importance in the chemistry of aromatic compounds, especially for the synthesis of aromatic fluoro compounds. However, the implementation of this reaction is accompanied by a range of process-related problems to which it has hitherto been impossible to find a satisfactory solution.

The reactions are generally carried out in the presence of a catalyst such as, for example, palladium, a solvent and an aqueous base such as, for example, sodium hydroxide solution. Under these reaction conditions the selectivities and yields for reductive dehalogenations of chlorinated/brominated fluorobenzenes are no more than moderate. As a rule, these reactions are difficult to reproduce (catalyst poisoning) and the selectivity is distinctly impaired by the elimination of fluorine. Chloride corrosion is in many cases unavoidable, since the majority of dehalogenations require reaction temperatures of more than 100° C.

The elimination of fluorine is accompanied by two principal problems which in many cases are insoluble. On the one hand, the purification of the crude products, which are formed with different fluoride contents, is virtually impossible or is possible only by a highly complex separation procedure, since their boiling points are in most cases virtually identical. On the other hand, the fluoride formed in the reaction may lead to further corrosion, which can only be countered by placing stringent requirements on the reactor material.

Moreover, the high nucleophilicity of the base used (e.g. aqueous NaOH) leads to the formation of phenols, further impairing the selectivity of this reaction. If the conventional mines are used, for example trimethylamine or triethylamine, the occurrence of secondary reactions can be suppressed to a very great extent. It is impossible or very difficult to recover the salts formed with these bases, or the free bases themselves, so that—in addition to high costs—there is considerable organic contamination of the waste water, and industrial implementation of the process is virtually prohibited.

In view of the large number of secondary reactions and the process-related problems of the preparation processes known to date, there is a great requirement for an improved synthesis option for the preparation of high-purity fluorobenzenes, the requirement being not only for good to very good yields but also for easily accessible precursors which are available on an industrial scale. The reductive elimination of chlorine appears to be a highly favorable preparation process but one which, because of the high corrosion, the unfavorable product quality and the difficulty of reproducing experiments (catalyst poisoning), has so far rarely been able to be converted to industry. There was therefore a great need to tackle the deficiencies which have been described and to develop an industrially favorable process.

The object is achieved by a process for the preparation of aromatic fluoro compounds of the formula (I)

$$F_nArR^1R^2R^3 \qquad (I)$$

in which
Ar is phenyl, naphthyl or pyridyl, $R^1$, $R^2$ and $R^3$ independently of one another are hydrogen, halide, preferably fluorine, chlorine or bromine $(C_1–C_4)$-alkyl, phenyl, $NR_2$, OR, CN, COH or COR, where R is hydrogen or $(C_1–C_6)$-alkyl, and n=1, 2, 3, 4 or 5, which comprises reacting aromatic fluoro compound of the formula (II)

$$X_mF_nArR^1R^2R^3 \qquad (II)$$

in which Ar, $R^1$, $R^2$, $R^3$ and n have the above-mentioned meaning, each X is a chlorine or bromine atom and m=1, 2, 3, 4 or 5, with hydrogen in the presence of a palladium catalyst, a water-insoluble amine which also does not form water-soluble hydrohalides, and if desired an inert solvent.

The starting compounds may be bromo or chloro compounds, for example:
4-chloro-1,2-difluorobenzene, 3-chloro-1,2-difluorobenzene, 2-chloro-1,4-difluorobenzene, 5-chloro-1,2,4-trifluorobenzene, 3-chloro-1,2,4-trifluorobenzene, 3-chloro-1,2,5-trifluorobenzene, 4-chloro-1,2,3-trifluorobenzene, 5-chloro-1,2,3-trifluorobenzene, 4-bromo-1,2-difluorobenzene, 3-bromo-1,2-difluorobenzene, 2-bromo-1,4-difluorobenzene, 5-bromo-1,2,4-trifluorobenzene, 3-bromo-1,2,4-trifluorobenzene, 3-bromo-1,2,5-trifluorobenzene, 4-bromo-1,2,3-trifluorobenzene, 5-bromo-1,2,3-trifluorobenzene or 5-chloro-2,3-difluoropyridine. The process my also employ mixtures of compounds of the formula (II) which, after reaction, result in a uniform compound of the formula (I) . In this context, these compounds can be employed with the same substitution pattern as the end compound, and also as mixtures of different chloro and bromo compounds.

This process is particularly advantageous for preparing 1,2,4-trifluorobenzene, 1,2,3-trifluorobenzene, 1,3-difluorobenzene, 1,2-difluorobenzene, 1,4-difluorobenzene and 2,3-difluoropyridine.

It is expedient to use the catalyst on a support material, for example activated charcoal, calcium carbonate, barium sulfate, pumice, argillaceous earth, kieselguhr, silica gel and/or alumina. Palladium is preferred, on activated charcoal or alumina as support material.

The palladium content of the supported catalyst is preferably from 0.1 to 10% by weight, preferably from 0.2 to 8% by weight and particularly preferably from 0.5 to 6% by weight of palladium, based on the overall catalyst.

The quantity of catalyst required is in the range from 0.01–50 mmol of palladium, based on the equivalents of halogen (chlorine/bromine) to be eliminated.

The catalyst can be recycled without difficulty, and thus used for more than one halogen elimination process.

The amines used can be monoamines or polyamines having from two to four amino groups, or mixtures thereof, with the proviso that both the free base and the base hydrohalide resulting from the HX which is formed are not soluble in water under the reaction and work-up conditions. Alkylamines have proved favorable in many cases.

Particularly suitable amines are those of the formula $$H_pN(C_rH_{2r+1})_q \qquad (III)$$

where p=0,1; q=1, 2 or 3 and p+q=3; r=5–20, preferably 8–15, and the alkyl radicals may be identical or different and linear or branched.

Highly effective aliphatic amines are specifically tri(n-dodecyl)amine and tri(iso-octyl) amine; and trialkyl($C_8/C_{10}$) amines or mixtures thereof.

Although the abovementioned trialkylamines of the stated formula (III) are the most suitable, it is also possible in principle to employ arylamines or aralkylamines.

Very good results are obtained if both the amines employed and the resulting hydrohalides are liquid.

In many cases it has proven advantageous to work with amine concentrations of from 50 to 500 mol % of amine per equivalent of halogen to be eliminated; the amine is employed in particular in quantities of 80–250 mol %, preferably 100–150 mol %, per equivalent of halogen to be eliminated.

If the starting materials and products used are compounds which are liquid at reaction and work-up temperature, it has been found favorable to work without an additional solvent. In the case of solid products the process can be carried out in the presence of an inert solvent, for example benzene, toluene, xylene, $(C_1–C_4)$-alkanols, such as methanol, ethanol or propanol, polyglycols such as ethylene glycol, dialkyl ethers such as diethyl ether or methyl ethyl ether, tetrahydrofuran, pentane, hexane, heptane or polyethers such as polyethylene glycol dimethyl ether 500, or mixtures of these solvents.

The presence of water in this process is not necessary. The reaction may be carried out in the presence of water, but it is advantageous to work with a minimal content of water, i.e. less than 5% by weight, and in particular less than 1% by weight, based on the overall reaction solution.

The reaction can be carried out either at atmospheric pressure or at superatmospheric pressure. It is expedient to carry out the reaction at a hydrogen overpressure of from 0.1 to 50 bar.

In many cases it has proven advantageous to carry out the process at temperatures of from 0° to 150° C., in particular from 40° C. to 120° C. The use of excessively low temperatures results in a slow and incomplete reaction. Too high a choice of temperature may in some cases lead to unwanted elimination of fluorine.

The aminehydrohalide formed at the end of the reaction can be simply and advantageously regenerated by treating the crude solution with aqueous base. This results, practically without loss, in the free amine which can be employed again without further pretreatment in the subsequent reaction, after separating off the product.

By precise neutralization of the aminehydrohalide, base is only consumed to the extent that equivalents of aromatic fluoro compound have formed. The resulting waste water gives a neutral reaction.

The used catalyst obtained in the reaction can be used further without treatment, or can be purified by known purification methods, for example using steam.

A particular advantage of the process according to the invention is that virtually no by-products are formed in the reaction, so that the remaining mother liquors and the forerunnings, intermediate runnings and residues from distillation can be recycled to the subsequent batches without danger of contamination. This makes the process extremely advantageous in ecological and economic terms.

The starting compounds for the process according to the invention can be prepared by nitrating the corresponding chlorinated fluorobenzenes or by chlorine/fluorine exchange reactions of chlorinated aromatic nitro compounds. If chlorinated aromatic fluoro compounds are required as starting compound, they can be prepared simply by means of denitrating chlorination of the corresponding fluorinated aromatic nitro compounds.

The process according to the invention is illustrated by the following examples, without being limited thereto.

EXAMPLE 1

For the preparation of 1,2,3-trifluorobenzene, 299.7 g (1.8 mol) of 4-chloro-1,2,3-trifluorobenzene, and 4.1 g of 5% Pd/C (50% water-moist) as catalyst, are placed, together with 846.3 g (2.12 mol) of tri ($C_8/C_{10}$)alkylamine as base, in a reaction vessel (autoclave). The reaction solution is heated to 75° C. and reductively dechlorinated with hydrogen at this temperature. After the uptake of hydrogen has ended, the reaction solution is stirred for a short time before being cooled to room temperature and neutralized with sodium hydroxide solution, and the catalyst is filtered off with suction from the reaction mixture. The organic phase is separated off and distilled at atmospheric pressure and the resulting distillate is dried and then fractionated. The remaining mother liquor, forerunnings, intermediate runnings and residues from distillation are recycled without further pretreatment to the subsequent batch.

Conversion: 95.1% (by GC)

Yield: 219.2 g (1.66 mol) of 1,2,3-trifluorobenzene 92.2% based on the 4-chloro-1,2,3-trifluorobenzene employed.

Purity: >99.9 (GC area-%) 1,2,3-trifluorobenzene

Subsequent batch

The amine mother liquor, together with the production residues from the initial batch, is made up with 299.7 g (1.8 mol) of 4-chloro-1,2,3-trifluorobenzene and 4.1 g of 5% Pd/C (50% water-moist) and, analogously to the initial batch, is reductively dechlorinated and worked up correspondingly.

The production residues resulting from the fractionation (forerunnings, intermediate runnings and residues from distillation) are recycled without further pretreatment to the subsequent batch.

Conversion: 98.1% (by GC)

Yield: 231.0 g (1.75 mol) of 1,2,3-trifluorobenzene 97.2% based on the 4-chloro-1,2,3-trifluorobenzene employed.

Purity: >99.9 (GC area-%) 1,2,3-trifluorobenzene

EXAMPLE 2

For the preparation of 1,2,4-trifluorobenzene, 299.7 g (1.8 mol) of 5-chloro-1,2,4-trifluorobenzene, and 4.1 g of 5% Pd/C (50% water-moist) as catalyst, are placed, together with 846.3 g (2.12 mol) of tri($C_8/C_{10}$)alkylamine as base, in a reaction vessel (autoclave). The reaction solution is heated to 90° C. and reductively dechlorinated with hydrogen at this temperature. After the uptake of hydrogen has ended, the reaction solution is stirred for a short time before being cooled to room temperature and neutralized with sodium hydroxide solution, and the catalyst is filtered off with suction from the reaction mixture. The organic phase is separated off and distilled at atmospheric pressure, and the resulting distillate is dried and then fractionated. The remaining mother liquor, forerunnings, intermediate runnings and residues from distillation are recycled without further pretreatment to the subsequent batch.

Conversion: 93.0% (by GC)

Yield: 214.7 g (1.63 mol) of 1,2,4-trifluorobenzene 90.3% based on the 5-chloro-1,2,4-trifluorobenzene employed.

Purity: >99.9 (GC area-%) 1,2,4-trifluorobenzene

Subsequent batch

The amine mother liquor, together with the production residues of the initial batch, is made up with 299.7 g (1.8 mol) of 4-chloro-1,2,4-trifluorobenzene and 4.1 g of 5% Pd/C (50% water-moist) and, analogously to the initial batch, is reductively dechlorinated and worked up correspondingly.

The production residues resulting from the fractionation (forerunnings, intermediate runnings and residues from distillation) are recycled without further pretreatment to the subsequent batch.

Conversion: 98.0% (by GC)

Yield: 228.1 g (1.72 mol) of 1,2,4-trifluorobenzene 96.0% based on the 4-chloro-1,2,4-trifluorobenzene employed.

Purity: >99.9 (GC area-%) 1,2,4-trifluorobenzene

EXAMPLE 3

For the preparation of 1,2-difluorobenzene, 360 g (2.2 mol) of a mixture of 47% chloro-1,2-difluorobenzenes (two isomers in a ratio of 1:3.5) and 52% dichloro-1,2-difluorobenzenes (two isomers in a ratio of 4.3:0.9), and 12.5 g of 5% Pd/C (50% water-moist) as catalyst, are placed, together with 1037.9 g (2.6 mol) of tri($C_8/C_{10}$) alkylamine as base, in a reaction vessel (autoclave). The reaction solution is heated to 65° C. and reductively dechlorinated with hydrogen at this temperature. After the uptake of hydrogen has ended, the reaction solution is stirred for a short time before being cooled to room temperature and neutralized with sodium hydroxide solution, and the catalyst is filtered off with suction from the reaction mixture. The organic phase is separated off and distilled at atmospheric pressure, and the resulting distillate is dried and then fractionated. The remaining mother liquor, forerunnings, intermediate runnings and residues from distillation can be recycled to subsequent batches.

Conversion: 98.0% (by GC) Yield: 211.7 g (1.86 mol) of 1,2-difluorobenzene 84.5% based on the mixture of chloro- and dichloro-1,2-difluorobenzenes employed.

Purity: >99.2 (GC area-%) 1,2-difluorobenzene

EXAMPLE 4

For the preparation of 2,3-difluoropyridine, 179.4 g (1.2 mol) of 5-chloro-2,3-difluoropyridine, and 4.5 g of 5% Pd/C (50% water-moist) as catalyst, are placed, together with 598.5 g (1.5 mol) of tri ($C_8/C_{10}$) alkylamine as base, in a reaction vessel (autoclave). The reaction solution is heated to 90° C. and reductively dechlorinated with hydrogen at this temperature. After the uptake of hydrogen has ended, the reaction solution is stirred for a short time before being cooled to room temperature and neutralized with sodium hydroxide solution, and the catalyst is filtered off with suction from the reaction mixture. The organic phase is separated off and distilled at atmospheric pressure, and the resulting distillate is dried and then fractionated. The remaining mother liquor, forerunnings, intermediate runnings and residues from distillation are recycled without further pretreatment to the subsequent batch.

Conversion: 95.0% (by GC)

Yield: 127.7 g (1.1 mol) of 2,3-difluoropyridine 91.7% based on the 5-chloro-2,3-difluoropyridine employed.

Purity: >99 (GC area-%) 2,3 -difluoropyridine

Subsequent batch

The amine mother liquor, together with the production residues from the initial batch, is made up with 179.4 g (1.2 mol) of 5-chloro-2,3-difluoropyridine and 4.5 g of 5% Pd/C (50% water-moist) and, analogously to the initial batch, is reductively dechlorinated and worked up correspondingly.

The production residues resulting from the fractionation (forerunnings, intermediate runnings and residues from distillation) are recycled without further pretreatment to the subsequent batch.

Conversion: 99.5% (by GC)

Yield: 135.6 g (1.18 mol) of 2,3-difluoropyridine 98.2% based on the 5-chloro-2,3-difluoropyridine employed.

Purity: >99.9 (GC area-%) 2,3-difluoropyridine

EXAMPLE 5

Initial batch

For the preparation of 1,3-difluorobenzene, 267.3 g (1.8 mol) of 4-chloro-1,3-difluorobenzene, and 4.1 g of 5% Pd/C (50% water-moist) as catalyst, are placed, together with 840.0 g (2.1 mol) of tri ($C_8/C_{10}$) alkylamine as base, in a reaction vessel (autoclave). The reaction solution is heated to 100° C. and reductively dechlorinated with hydrogen at this temperature. After the uptake of hydrogen has ended, the reaction solution is stirred for a short time before being cooled to 20°–25° C. and adjusted to pH 7–8 with sodium hydroxide solution, and the catalyst is filtered off with suction from the reaction mixture. The organic phase is separated off and distilled at atmospheric pressure, and the resulting distillate is dried and then fractionated. The remaining residue from distillation and the forerunnings and intermediate runnings are recycled without further pretreatment to the subsequent reaction.

Conversion: 95.1% (by GC)

Yield: 189.1 g (0.82 mol) of 1,3-difluorobenzene 92.12% based on the 4-chloro-1,3-difluorobenzene employed.

Purity: >99.9 (GC area-%) 1,3-difluorobenzene

Subsequent batch

The amine mother liquor, together with the production residues from the initial batch, is made up with 267.3 g (1.8 mol) of 4-chloro-1,3-difluorobenzene and 4.1 g of 5% Pd/C (50% water-moist) and, analogously to the initial batch, is reductively dechlorinated and worked up correspondingly.

The production residues resulting from the fractionation (forerunnings, intermediate runnings and residues from distillation) are recycled without further pretreatment to the subsequent batch.

Conversion: 98.1% (by GC)

Yield: 201.5 g (1.77 mol) of 1,3-difluorobenzene 98.1% based on the 4-chloro-1,3 -difluorobenzene employed.

Purity: >99.9 (GC area-%) 1,3-difluorobenzene

We claim:

1. A process for the preparation of aromatic fluoro compounds of the formula I $$R_n ArR^1 R^2 R^3 \quad (I)$$

in which

Ar is phenyl, naphthyl or pyridyl, $R^1$, $R^2$ and $R^3$ independently of one another are hydrogen, halide ($C_1$–$C_4$)-alkyl, phenyl, $NR_2$, OR, CN, COH or COR, where R is hydrogen or ($C_1$–$C_6$)-alkyl, and n=1, 2, 3, 4 or 5, which comprises reacting aromatic fluoro compounds of the formula II $$X_m F_n ArR^1 R^2 R^3 \quad (II)$$

in which Ar, $R^1$, $R^2$, $R^3$ and n have the above-mentioned meaning, each X is a chlorine or bromine atom and m=1, 2, 3, 4 or 5, with hydrogen in the presence of a palladium catalyst, a water-insoluble amine which also does not form water-soluble hydrohalides, and if desired an inert solvent.

2. The process as claimed in claim 1, which comprises using 4-chloro-1,2-difluorobenzene, 3-chloro-1,2-difluorobenzene, 2-chloro-1,4-difluorobenzene, 5-chloro-1,2,4-trifluorobenzene, 3-chloro-1,2,4-trifluorobenzene, 3-chloro-1,2,5-trifluorobenzene, 4-chloro-1,2,3-trifluorobenzene, 5-chloro-1,2,3-trifluorobenzene, 4-bromo-1,2-difluorobenzene, 3-bromo-1,2-difluorobenzene, 2-bromo-1,4-difluorobenzene, 5-bromo-1,2,4-trifluorobenzene, 3-bromo-1,2,4-trifluorobenzene, 3-bromo-1,2,5-trifluorobenzene, 4-bromo-1,2,3-trifluorobenzene, 5-bromo-1,2,3-trifluorobenzene or 5-chloro-2,3-difluoropyridine as suitable aromatic fluoro compounds of the formula (II).

3. The process as claimed in claim 1, which comprises employing mixtures of compounds of the formula (II) which result, after reaction, in a uniform compound of the formula (I).

4. The process as claimed in claim 1, which comprises preparing 1,2,4-trifluorobenzene, 1,2,3-trifluorobenzene, 1,2-difluorobenzene, 1,3-difluorobenzene, 1,4-difluorobenzene or 2,3-difluoropyridine.

5. The process as claimed in claim 1, wherein said reaction is carded out at temperatures of from 0° to 1500° C.

6. The process as claimed in claim 1, wherein the quantity of water in the reaction solution is less than 5% by weight, based on the overall reaction solution.

7. The process as claimed in claim 1, wherein the palladium catalyst is employed in a support material.

8. The process as claimed in claim 7, wherein the support material employed is selected from the group consisting of activated charcoal, calcium carbonate, barium sulfate, pumice, argillaceous earth, kieselguhr, silica gel, and alumina or a mixture thereof.

9. The process as claimed in claim 7, wherein the catalyst contains 0.1–10% by weight of palladium, based on the support material used.

10. The process as claimed in claim 1, wherein the catalyst employed is from 0.01 to 50 mmol of palladium, based on equivalents of halogen to be eliminated.

11. The process as claimed in claim 1, wherein the catalyst is recycled.

12. The process as claimed in claim 1, wherein the amines employed are alkylamines.

13. The process as claimed in claim 1, wherein the amine employed is an amine of the formula (III)

  (III)

where p=0.1; q=1, 2 or 3; p+q=3 and r=5–20, radicals may be identical or different and linear or branched.

14. The process as claimed in claim 1, wherein the amines used are tri(n-dodecyl)amine, tri(iso-octyl)amine, tri-alkyl($C_8$/$C_{10}$)amines or mixtures of these amines.

15. The process as claimed in claim 1, wherein the aliphatic amines used are liquid in the reaction medium at reaction and work-up temperature.

16. The process as claimed in claim 1, wherein the hydrohalides resulting from the aliphatic amines are liquid in the reaction medium.

17. The process as claimed in claim 1, wherein the alkylamine is used in quantities of 50–500 mol % based on equivalents of halogen to be eliminated.

18. The process as claimed in claim 1, wherein said reaction is carried out at atmospheric or superatmospheric pressure.

19. The process as claimed in claim 1, wherein the solvents employed are benzene, toluene, xylene, ($C_1$–$C_4$)-alkanols, polyglycols, dialkyl ethers, polyethers or mixtures of these solvents.

20. The process as claimed in claim 1, wherein the amine is recycled.

21. The process as claimed in claim 1, wherein all the production residues are recycled to the subsequent batch.

22. The process as claimed in claim 4, wherein said reaction is carried out at temperatures of from 40° to 120° C., the quantity of water in the reaction solution is less than 1 by weight based on the overall reaction solution and the support material is activated charcoal or alumina.

23. The process as claimed in claim 22, wherein the catalyst contains 0.5–6% by weight of palladium, based on the support material used and r is 8–15.

24. The process as claimed in claim 17, wherein the alkyl amine is used in quantities of 100–150 mmol % based on the equivalents of halogen to be eliminated and is carried out at a hydrogen overpressure of from 0.5 to 50 bar.

25. The process as claimed in claim 1, wherein the alkyl amine is used in quantities of from 80–250 mmol % based on the equivalents of halogen to be eliminated and the solvents employed are selected from the group consisting of methanol, ethanol, propanol, ethylene glycol, diethyl ether, methyl ethyl ether, tetrahydrofuran, pentane, hexane or heptane or polyethylene glycol dimethyl ether 500 and the catalyst contains 0.2–8% by weight of palladium based on the support material used.

* * * * *

UNITED STATES PATENT AND TRADEMARK OFFICE
CERTIFICATE OF CORRECTION

PATENT NO. : 5,498,807
DATED : March 12, 1996
INVENTOR(S) : Schach et al

It is certified that error appears in the above-indentified patent and that said Letters Patent is hereby corrected as shown below:

In column 4, line 10, the phrase "p = 0.1;" should read --p = 0, 1 or 2;-- thereof.

In column 8, line 10, the phrase "$R_nArR^1R^2R^3$" should read --$F_nArR^1R^2R^3$-- thereof.

In column 8, line 13, the phrase "halide ($C_1$-$C_4$)-alkyl" should read --halide, ($C_1$-$C_4$)-alkyl-- thereof.

In column 8, line 49, the word "carded" should read --carried-- thereof.

In column 8, line 49, the phrase "1500°C" should read --150°C-- thereof.

In column 9, line 8, the phrase "p = 0.1;" should read --p = 0, 1 or 2;-- thereof.

Signed and Sealed this

Fifteenth Day of October, 1996

Attest:

BRUCE LEHMAN

*Attesting Officer*   *Commissioner of Patents and Trademarks*